(12) United States Patent
Washington

(10) Patent No.: US 6,997,394 B1
(45) Date of Patent: Feb. 14, 2006

(54) DOOR KNOB-MOUNTED AIR FRESHENER DEVICE

(76) Inventor: Evie Washington, 322 Linkview Dr., Duncanville, TX (US) 75137

( * ) Notice: Subject to any disclaimer, the term of this patent is extended or adjusted under 35 U.S.C. 154(b) by 0 days.

(21) Appl. No.: 10/957,023

(22) Filed: Oct. 4, 2004

(51) Int. Cl.
B05B 15/00 (2006.01)
(52) U.S. Cl. ............... 239/274; 239/289; 239/239; 239/320; 239/321; 239/322; 239/333; 222/192; 222/386
(58) Field of Classification Search ............... 239/274, 239/289, 320, 321, 322, 327, 333; 222/192, 222/209, 215, 386; 16/404, 412, 414
See application file for complete search history.

(56) References Cited

U.S. PATENT DOCUMENTS

| | | | |
|---|---|---|---|
| 1,633,988 A | | 6/1927 | Jones |
| 2,817,560 A | * | 12/1957 | Barnard et al. ............. 239/327 |
| 3,994,440 A | * | 11/1976 | Mancini ..................... 239/274 |
| 4,082,351 A | | 4/1978 | Chrones |
| 4,914,554 A | | 4/1990 | Sowers |
| 5,008,551 A | | 4/1991 | Randolph |
| 5,060,864 A | * | 10/1991 | Nishi et al. ................. 239/289 |
| 5,495,641 A | | 3/1996 | Going et al. |
| 5,967,412 A | * | 10/1999 | Lee ............................. 239/57 |

* cited by examiner

Primary Examiner—Steven J. Ganey
(74) Attorney, Agent, or Firm—Donald R. Schoonover

(57) ABSTRACT

An air freshener dispenser mechanism is incorporated into a door knob whereby when a door is pushed open, air freshener is dispensed into a room in advance of a person entering the room.

2 Claims, 1 Drawing Sheet

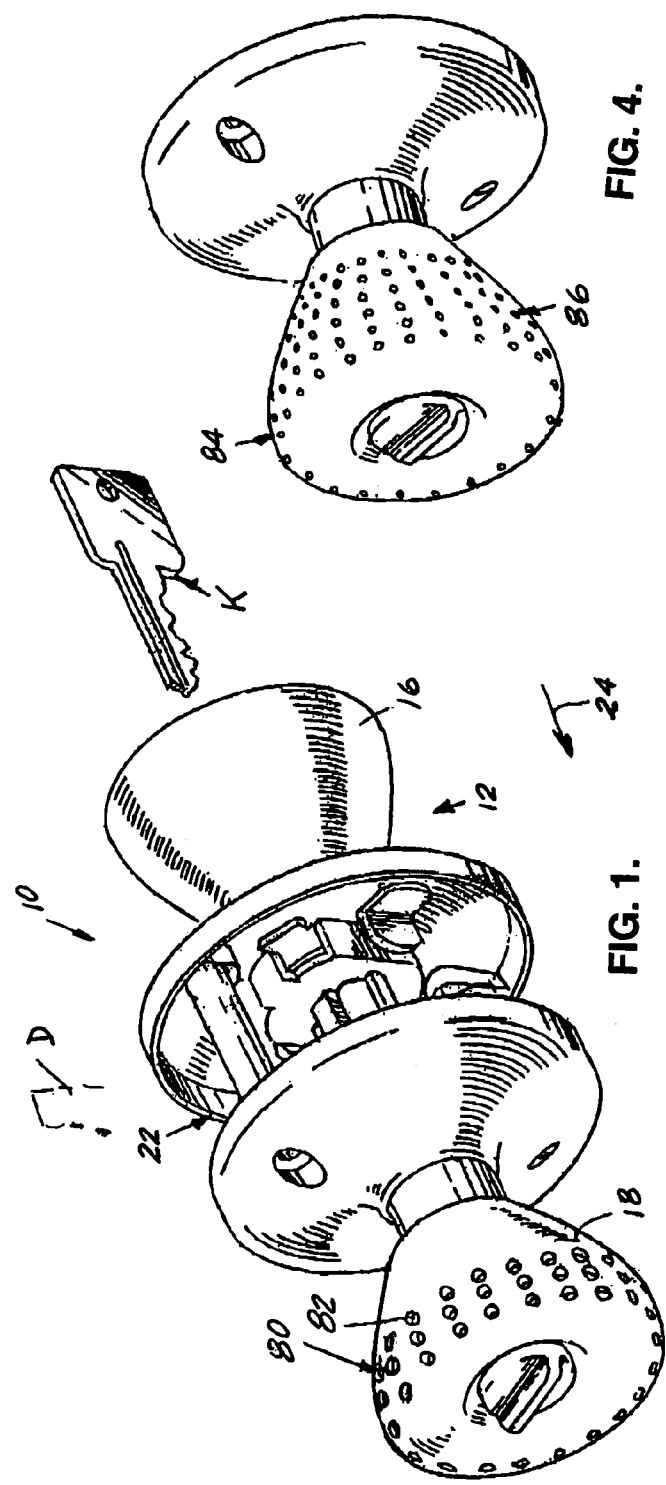
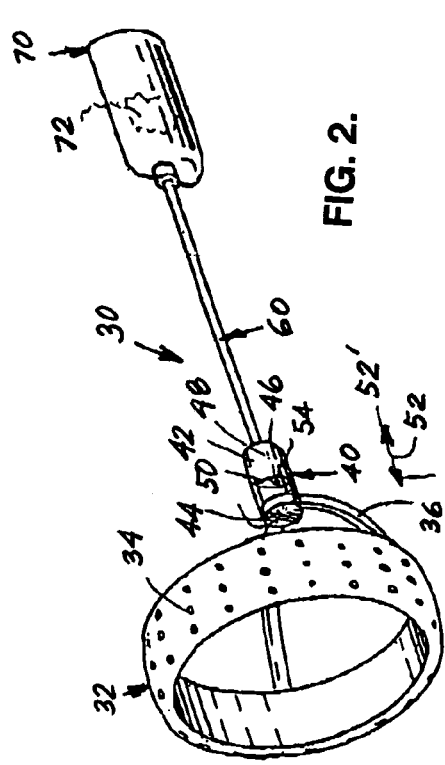

DOOR KNOB-MOUNTED AIR FRESHENER DEVICE

BACKGROUND OF THE INVENTION

1. Field of the Invention

The present invention relates to the general art of dispensing, and to the particular field of air freshener dispensers combined with other devices.

2. Description of the Related Art

Fragrances and scents for use in freshening the air in a room are well known in the art and the art contains many examples of such devices. These devices range from simple containers that are opened to allow evaporation to dispense the aroma, to complex devices that include fans, motors, and the like.

When a person initially enters a room, one of the first things they notice is the smell of the room. If a room is musty, or has cooking odors, or smoke odors, or the like, this is immediately noticed by a person entering the room. For this reason, many air freshener devices operate continuously so people entering a room notice the freshened smell rather than some other, less pleasing, smell. However, this can be wasteful if the room is unoccupied for a long time. Fragrance dispensed into an empty room is generally wasted.

Therefore, there is a need for a dispenser for dispensing air freshening ingredients into a room, but only when such air freshening is needed.

Since initial entry into a room is when fragrance is most noticed, the most effective time to have fragrance dispensed is when someone is most likely to be initially entering a room.

Therefore, there is a need for a dispenser for dispensing air freshening ingredients into a room, but only when such air freshening is needed and when such dispensing is most effective.

While the art has air freshener dispensers attached to doors, such device depend on the movement of the door to dispense the air freshener. Once a door is moving, the person is nearly always into the room, and the fragrance dispensed will not be as effective as it would be if the fragrance were dispensed before the person entered the room. Once a person enters a room, it does not take long for their olfactories to become used to the scent in a room and air freshener dispensed at this time will not be as effective.

The inventor is not aware of any air freshener dispenser that will overcome the just-mentioned difficulty and dispense air freshener only when needed and in the most effective manner and do so before a person enters a room.

Therefore, there is a need for an air freshener device that will dispense air freshener only when needed and in the most effective manner and do so before a person enters a room.

PRINCIPAL OBJECTS OF THE INVENTION

It is a main object of the present invention to provide a dispenser for dispensing air freshening ingredients into a room, but only when such air freshening is needed.

It is another object of the present invention to provide a dispenser for dispensing air freshening ingredients into a room, but only when such air freshening is needed and when such dispensing is most effective.

It is another object of the present invention to provide an air freshener device that will dispense air freshener only when needed and in the most effective manner and do so before a person enters a room.

SUMMARY OF THE INVENTION

These, and other, objects are achieved by an air freshener device that is incorporated into the door knob of a door and which is operated to dispense fragrance when the door is being pushed open. The air freshener is dispensed into a room immediately prior to a person entering the room, and the movement of the door will enhance the dispensing operation by causing air currents directed into the room to assist in the dispersing of the air freshener.

Using the air freshener device embodying the present invention will permit a fragrance to be dispersed immediately before a person enters a room, but only at that time. Thus, fragrance is dispersed efficiently and is not wasted and is dispersed in a manner that is most effective.

BRIEF DESCRIPTION OF THE DRAWING FIGURES

FIG. 1 is a perspective view of an air freshener device embodying the present invention.

FIG. 2 is a perspective of an air freshener dispensing mechanism used in the air freshener device embodying the present invention.

FIG. 3 is a perspective view of an alternative form of a door knob element used in the air freshener device embodying the present invention.

FIG. 4 is a perspective view of an alternative form of a door knob element used in the air freshener device embodying the present invention.

DETAILED DESCRIPTION OF THE PREFERRED EMBODIMENT

Other objects, features and advantages of the invention will become apparent from a consideration of the following detailed description and the accompanying drawings.

Referring to the Figures, it can be understood that the present invention is embodied in an air freshener device 10 that is contained in a handle mechanism associated with a door of a room and which is operated when the door is moved into a room to dispense scent into the room as the door is being moved into the room. For purposes of this disclosure, movement of the door into a room will be referred to as opening the door.

Device 10 comprises a door knob unit 12 mounted on a door, indicated as door D in FIG. 1. Other than the structure that will be described herein, unit 12 is mounted on door D in the usual manner and such mounting will not be described in detail.

Door knob unit 12 includes a first handle 16 that is located on the outside of a room in a use condition and into which a key K is inserted to open the door. Unit 12 further includes a second handle 18 that is located inside a room in a use condition. A connecting element 22 connects first handle 16 to second handle 18 and which extends through door D on which the first and second handles 16, 18 are mounted so the handles 16, 18 can be operated in a manner well known to those skilled in the art.

First handle 16 is movably mounted on connecting element 22 to move toward the door when the first handle is pushed toward the door as indicated in FIG. 1 by arrow 24. First handle 16 can include spring elements to move it in the opposite direction after the handle is released, or it can simply remain in a forward position until a person grasps the handle and moves it in the direction opposite to direction 24.

A scent dispersing unit 30 is mounted on second handle 18 and operates to dispense room air freshener material into a room as handle unit 12 is pushed to open the door into the room. Scent dispersing unit 30 includes a cover 32 which is mounted on second handle 18, a plurality of outlet ports, such as outlet port 34, defined through the cover 32, and a manifold 36 fluidically connected to the outlet ports 34 and located inside second handle 18.

Scent dispersing unit 30 further includes a pump mechanism 40 located inside second handle 18 and which is fluidically connected to manifold 36. Pump mechanism 40 includes a hollow housing 42 having a first end 44 located adjacent to second handle 18, a second end 46 spaced apart from first end 44, and a longitudinal axis 48 extending between first end 44 and second end 46.

A piston 50 is movably mounted inside hollow housing 42 to move in the direction of longitudinal axis 48 toward and away from first end 44 as indicated by arrow 52. A one-way valve 54 is located in the piston 50 and opens to define a fluid passageway through the piston 50 when the piston 50 moves away from first end 44 in direction 52' and closes to occlude the fluid passageway through the piston 50 when piston 50 moves toward second end 46 in direction 52". The one-way valve is known to those skilled in the art and thus will not be further discussed in detail.

A rigid fluid feed line 60 is fluidically and mechanically connected to piston 50 and extends through connecting element 22. Fluid line 60 is movably mounted in connecting element 22 to move in association with movement of first handle 16 toward and away from second handle 18 in directions 52' and 52" with direction 52" corresponding to direction 24.

A fluid reservoir 70 is located in first handle 16 and is fluidically connected to fluid feed line 60. A fluid scent 72 is stored in fluid reservoir 70 to be drawn into housing 42 when piston 50 moves in direction 52" and to be forced into manifold 36 when piston 50 moves in direction 52". One-way valve 52 closes when piston 50 moves in direction 52" to force fluid scent 72 out of housing 42 and into manifold 36 to be forced out of manifold 36 via ports 34, and opens when piston 50 moves in direction 52' to draw fluid scent 72 into housing 42 from reservoir 70 via fluid line 60. Reservoir 70 is rigid and is rigidly connected to first handle 16 to move therewith. Since fluid line 60 is also rigid, movement of handle 16 will be mechanically transmitted to piston 50. Reservoir 70 is removed from handle 16 and from fluid line 60, and replaced when scent material 72 is depleted. To this end, handle 16 has elements that removably attach it to the door.

One form of scent dispensing unit 30 is shown in FIG. 1 to include a cover 80 that has outlet ports, such as outlet port 82, fluidically aligned with outlet ports 34 of cover 32. Another form of unit 30 includes a cover 84 shown in FIG. 4 that has a plurality of outlet ports, such as outlet port 86. Yet another form of unit 30 includes a pump unit 90 that is shown in FIG. 3. Pump unit 90 includes a plurality of compressible beads, such as bead 92, mounted on a cover 94 that is shaped and sized to be accommodated on first handle 16. The beads 92 are fluidically connected together and to fluid line 60. As a user grasps handle 16, the beads 92 are compressed to force fluid scent 72 out of the beads 92 into fluid line 60. In the case of pump unit 90, a pump mechanism 40 is not used since the pumping action occurs when a user compresses the beads 92; however, the remaining elements of the pump unit 90 correspond to the above-described elements of unit 30. When the beads 92 are depleted of scent material, the entire unit 90 can be replaced.

It is understood that while certain forms of the present invention have been illustrated and described herein, it is not to be limited to the specific forms or arrangements of parts described and shown.

What is claimed is:

1. An air freshener device comprising:
   (a) a door knob unit mountable on a door, said door knob unit including
      (1) a first handle that is located on the outside of a room in a use condition, a second handle that is located inside a room in a use condition, a connecting element connecting the first handle to the second handle and which extends through a door on which the first and second handles are mounted, and
      (2) the first handle being movably mounted on the connecting element to move toward the door when the first handle is pushed toward the door;
   (b) a scent dispersing unit mounted on the second handle, said scent dispersing unit including
      (1) a cover which is mounted on the second handle,
      (2) a plurality of outlet ports defined through the cover,
      (3) a manifold fluidically connected to the outlet ports and located inside the second handle,
      (4) a pump located inside the second handle and fluidically connected to the manifold, the pump including
         (A) a hollow housing, the hollow housing having a first end located adjacent to the second handle and a second end spaced apart from the first end, and a longitudinal axis extending between the first end of the hollow housing and the second end of the hollow housing,
         (B) a piston movably mounted inside the hollow housing to move in the direction of the longitudinal axis of the hollow housing toward and away from the first end of the hollow housing, and
         (C) a one-way valve in the piston that opens to define a fluid passageway through the piston when the piston moves away from the first end of the hollow housing and closes to occlude the fluid passageway when the piston moves toward the second end of the housing,
      (5) a rigid fluid feed line fluidically and mechanically connected to the piston of the pump and extending through the connecting element, the fluid line being movably mounted in the connecting element to move in association with movement of the first handle toward and away from the second handle, and
      (6) a fluid reservoir located in the first handle and which is fluidically connected to the fluid feed line; and
   (c) a fluid scent stored in the fluid reservoir.

2. An air freshener device comprising:
   (a) a door knob unit mountable on a door, said door knob unit including a first handle that is located on the outside of a room in a use condition, a second handle that is located inside a room in a use condition, a connecting element connecting the first handle to the second handle and which extends through a door on which the first and second handles are mounted;
   (b) a scent dispersing unit mounted on the second handle, said scent dispersing unit including a pump which is operatively connected to the first handle;
   (c) a fluid reservoir which is mounted in the first handle and is fluidically connected to said scent dispersing unit; and
   (d) a fluid scent stored in the fluid reservoir.

* * * * *